United States Patent
Sze et al.

(10) Patent No.: US 6,593,706 B1
(45) Date of Patent: Jul. 15, 2003

(54) HIGH PRESSURE NEON ARC LAMP

(75) Inventors: Robert C. Sze, Santa Fe, NM (US); Irving J. Bigio, Chestnut Hill, MA (US)

(73) Assignee: The Regents of the University of California, Oakland, CA (US)

( * ) Notice: Subject to any disclaimer, the term of this patent is extended or adjusted under 35 U.S.C. 154(b) by 16 days.

(21) Appl. No.: 09/968,829

(22) Filed: Oct. 2, 2001

(51) Int. Cl.⁷ .............................................. H05B 41/16
(52) U.S. Cl. ....................... 315/246; 315/56; 313/570; 607/88
(58) Field of Search ................................. 315/246, 348, 315/56, 58, 59, 224, 219; 313/567, 568, 570, 572, 634; 607/88–95; 604/20

(56) References Cited

U.S. PATENT DOCUMENTS

| | | | |
|---|---|---|---|
| 4,461,981 A | * 7/1984 | Saikatsu et al. | ............ 315/246 |
| 5,140,221 A | * 8/1992 | Ichinose | ...................... 313/581 |
| 5,153,479 A | * 10/1992 | Chakrabarti et al. | ........ 313/493 |
| 5,511,563 A | * 4/1996 | Diamond | .................... 128/898 |
| 6,130,511 A | 10/2000 | Rothwell, Jr. et al. | ...... 315/246 |
| 6,153,982 A | * 11/2000 | Reiners | ...................... 315/248 |
| 6,181,075 B1 | 1/2001 | Doss | .......................... 315/224 |

* cited by examiner

*Primary Examiner*—Don Wong
*Assistant Examiner*—Ephrem Alemu
(74) *Attorney, Agent, or Firm*—Madson & Metcalf

(57) ABSTRACT

A high pressure neon arc lamp and method of using the same for photodynamic therapies is provided. The high pressure neon arc lamp includes a housing that encloses a quantity of neon gas pressurized to about 500 Torr to about 22,000 Torr. At each end of the housing the lamp is connected by electrodes and wires to a pulse generator. The pulse generator generates an initial pulse voltage to breakdown the impedance of the neon gas. Then the pulse generator delivers a current through the neon gas to create an electrical arc that emits light having wavelengths from about 620 nanometers to about 645 nanometers. A method for activating a photosensitizer is provided. Initially, a photosensitizer is administered to a patient and allowed time to be absorbed into target cells. Then the high pressure neon arc lamp is used to illuminate the target cells with red light having wavelengths from about 620 nanometers to about 645 nanometers. The red light activates the photosensitizers to start a chain reaction that may involve oxygen free radicals to destroy the target cells. In this manner, a high pressure neon arc lamp that is inexpensive and efficiently generates red light useful in photodynamic therapy is provided.

19 Claims, 5 Drawing Sheets

HIGH PRESSURE NEON ARC LAMP

GOVERNMENT RIGHTS

This invention was made with Government support under Contract No. W-7405-ENG-36 awarded by the United States Department of Energy to The Regents of the University of California. The Government has certain rights in the invention.

BACKGROUND OF THE INVENTION

1. Field of the Invention

The present invention relates to arc lamps. More specifically, the invention relates to a high pressure neon arc lamp configured to efficiently produce incoherent light having wavelengths between about 625 nanometers and about 645 nanometers.

2. Relevant Technology

Light is a form of electromagnetic energy. Electromagnetic energy is divided into different spectrums based on the wavelength of the electromagnetic energy. Visible light is one of these spectrums. Within the visible light spectrum, light wavelengths may be identified by color. For example, light having wavelengths between about 625 nanometers and 645 nanometers appear to an observer as red. Electromagnetic energy with shorter wavelengths than visible light comprise the ultra-violet (UV) band of the spectrum. Electromagnetic energy with longer wavelengths than visible light comprise the infrared band of the spectrum.

Producing and using visible light is well understood. For example, it is conventional to produce light of different wavelengths using a variety of techniques such as incandescent, fluorescent, and arc lamps. It is also conventional to split or separate the different colors in light using a prism. Light can also be focused and intensified using conventional laser technology.

Visible light serves some important uses. Light is useful for interior and exterior lighting, traffic signals, tanning of skin, as well as a variety of other uses. Additionally, light is useful in medicine. Concentrated coherent light in the form of lasers provides very precise cutting tools for surgeons.

One field of medicine involves the use of light in a way other than as a high precision cutting tool. Photodynarnic therapy (PDT) is a medical treatment that uses visible light to activate a drug designed to destroy particular cells within a patient's body. PDT is becoming very popular. Generally, PDT involves a two part procedure for treating infectious diseases as well as cancer.

PDT begins by administering to a patient a drug known as a photosensitizer. Photosensitizers are drugs that are specifically engineered to target a particular kind of cell and tissue within the patient. Several photosensitizers are known including proprietary drugs such as Photofrin®. Generally, the photosensitizer is administered by injection. The photosensitizer may enter into, attach to, or surround the targeted cells and/or tissues. By way of example, PDT used to treat cancer involves photosensitizers that enter into the cancerous cells. The administration of the photosensitizer is completely harmless to the patient.

Next, PDT involves illuminating the target tissue, such as cancer cells, with a non-thermal, low powered light. Generally, this light should be red having wavelengths between 625 nanometers and 645 nanometers. Illumination of the target tissue with red light activates the photosensitizer to destroy the target tissue. Conventionally, the light source used is a low power laser.

Light of the red wavelength activates the photosensitizer concentrated in and around the target cells. In cancerous cells, the photosensitizer cooperates with oxygen to create an oxygen free-radical that destroys the cancerous cell. Because the photosensitizer exists primarily in the cancerous cells, the healthy cells remain unharmed. Unlike radiation therapy, PDT may be repeated with little recuperation time required for the patient. PDT may also be used to treat acne, remove unwanted hair, and in other applications. Generally, the effectiveness of PDT treatment depends on the amount of photosensitizer administered and the ability to illuminate enough of the photosensitizer at an appropriate intensity.

Generally, low powered, non-thermal lasers are used to activate the photosensitizer. There are several limitations to using lasers in PDT. Chief among the limitations of low powered, non-thermal lasers is the small area of illumination. Due to the nature of lasers and the manner in which they are generated, a very concentrated and small laser beam is generally created. Consequently, the laser beam has a small illumination area. Techniques exist to diffuse the laser light. However, such diffusion decreases the tissue penetration capability of the laser beam. The laser beam loses intensity. A small illumination area requires that the laser beam make several sweeps of an infected or cancerous area to illuminate the target cells. This increases the time required for treatment and may result in areas of tissue not being illuminated due to human error.

The limitation due to small illumination area is compounded when PDT is used to treat anti-biotic resistant infectious diseases of the skin. These diseases may cover large areas of a patient's skin. Thus, it is difficult to adequately treat these diseased areas using a laser with a small beam area. Effective treatment of the disease using PDT with lasers may require repeated illumination treatments.

Additionally, lasers are relatively expensive because by definition they produce coherent light. Coherent light is light in which all the photons are in phase. The cost is also high due to high power requirements for lasers. The expense used to produce coherent laser light is largely wasted when used for PDT.

PDT requires only a particular wavelength of photons to function. Coherency of the light is not a requirement. The photosensitizer is activated by the wavelength of the light. Generally, photosensitizers are activated regardless of the coherency of the light.

Additionally, lasers are generally very large and bulky in comparison to other medical equipment. Often, the portability of these devices is limited. Generally, the patient must be brought to the laser rather than the laser to the patient. Lasers may also require specialized training to operate.

PDT may also be used with incoherent light sources such as high pressure xenon or krypton arc lamps. A high pressure arc lamp is a lamp that creates light by passing an electrical arc between two electrodes through a specific gas. With high pressure xenon and krypton arc lamps the gas between the electrodes is pressurized to several hundred Torr. The gas is also substantially pure xenon or krypton. Generally, a xenon and krypton arc lamp provides a greater illumination area because the light is diffuse.

Xenon and krypton arc lamps however do not efficiently produce high intensity red light having wavelengths between 625 nanometers and 645 nanometers. The light generated by xenon and krypton arc lamps has wavelengths ranging from red to ultraviolet (UV). The majority of the light photons generated by xenon and krypton arc lamps are in the UV band of the electromagnetic spectrum. To provide the red light needed for PDT, the UV light is filtered out from the xenon and krypton arc lamp's output. UV light is also filtered to avoid burning the tissue of the patient. Because a majority of the light produced by a xenon or krypton arc lamp is filtered, the lamps are generally very inefficient.

Accordingly, what is needed is a high pressure arc lamp that efficiently produces photons in the red band of the electromagnetic spectrum, light having wavelengths between 625 nanometers and 645 nanometers, with minimal power requirements. Additionally, what is needed is a high pressure neon arc lamp that is less expensive to fabricate than conventional laser devices. Further, what is needed is a high pressure neon arc lamp that provides a comparably large illumination area at an operable intensity when compared to convention red light sources such as lasers. Such an invention is disclosed and claimed herein.

SUMMARY OF THE INVENTION

The invention is a high pressure neon arc lamp and method for using the lamp in photodynamic therapy. Conventionally, lasers, and xenon or krypton arc lamps are used in photodynamic therapy to provide a red light to activate photosensitive drugs within a patient to kill cells of cancer or other infectious diseases. However, xenon and krypton arc lamps produce mostly ultra-violet light rather than red light. Lasers can produce red light but are expensive and generally illuminate only a small area of tissue. The small illumination area of lasers may require multiple laser treatments to activate all the photosensitive drug in the patient. The present invention resolves these problems by producing mostly red light and illuminating a larger area than most lasers.

The high pressure neon arc lamp is a light source that may be configured to use a conventional electrical wall outlet. The high pressure neon arc lamp produces more red light at a higher intensity than xenon or krypton arc lamps. The high pressure neon arc lamp may also be smaller and cheaper to produce than conventional red lasers.

The high pressure neon arc lamp includes a sealed housing. Preferably, the sealed housing is translucent and configured to seal a quantity of substantially pure neon gas inside. Neon gas is used because its spectral signature is mostly light of red wavelengths. The spectral signature is a unique set of light wavelengths emitted when an atom of a particular element gains or loses energy.

The neon is preferably pressurized to between about 500 and about 22,000 Torr. The housing includes a bore that preferably extends coaxially within the housing. The pressurized neon gas is stored within the bore. The bore allows an electrical arc emitting red light to travel through the neon.

Preferably, the sealed housing is cylindrical. A cylindrical housing is inexpensive to fabricate and allows for a large electrical arc to pass through the bore. The longer the electrical arc, the larger the area that is illuminated by the lamp. A cylindrical shape also provides an effective container for neon gas at the pressures mentioned above. In a preferred embodiment, the diameter of the bore is consistent along the bore's entire length.

The sealed housing includes a first electrode and a second electrode installed on each end. The first electrode and second electrode provide an electrical path between an area outside the housing and the bore within the housing. The first electrode and second electrode are configured to facilitate passing of an electrical arc through neon gas within the bore.

The sealed housing is electrically coupled by the first electrode and second electrode to a voltage source. Preferably, the voltage source is a pulse generator configured to deliver a voltage in the range of 24 kilovolts to 30 kilovolts between the first electrode and the second electrode. Alternatively, the voltage source may supply a constant voltage between the first electrode and the second electrode. One voltage source provides a voltage pulse to overcome electrical impedance of the neon gas of the bore and a subsequent voltage source passes an electrical arc between the first electrode and the second electrode.

The pulse generator may be configured to provide a pulse of voltage at a rate influenced by the average power desired. The higher the average power, the higher the pulse repetition rate. The voltage pulse rate provides a sensitive technique for adjusting the average light power. Each pulse of voltage preferably creates an electrical arc between the first electrode and the second electrode. The electrical arc produces photons having wavelengths between about 575 nanometers and about 695 nanometers.

The present invention includes a method of using the high pressure neon arc lamp as a photosensitive drug activation device. Photosensitive drugs (also known as photosensitizers) are drugs which are activated by light, particularly light of specific wavelengths. The effect of activation of the drug depends largely on how the drug is engineered.

For example, photosensitive drugs used to treat cancer are designed to enter into the cancerous cells of a patient prior to activation of the drug. Photosensitive drugs used to treat cancer are generally activated using light having red wavelengths. The light interacts with the drug to generate an oxygen free radical. The oxygen free radical is created within the cancer cell. The membrane of the cancer cell is ruptured by the oxygen free radical. Thus, the cancer cell is destroyed.

According to a first step of the method, a photosensitive drug is administered to a patient. Generally administration of the drug is done intravenously to allow the drug to quickly attach to, enter, or surround target cells within the patient. The target cells are those that are unwanted.

Next, the photosensitive drug is allowed to be absorbed by target tissue such as cancer cells within the patient. The time for absorption may be a few hours to as long as a day or two. As the drug begins the be absorbed the patient must avoid premature exposure to light of red wavelengths. Premature exposure may activate the drug before it has singled out the target tissue. Generally, the patient must stay in-doors away from sunlight.

Then, target tissue is illuminated by the high pressure neon arc lamp to activate the photosensitizer drug and destroy the target cells. The high pressure neon arc lamp may be brought to the patient. The high pressure neon arc lamp illuminates such as large area that a single pass of the light may be all that is necessary. Additionally, because the procedure is non-invasive the patient may return to normal activities the same day.

These and other features and advantages of the present invention will become more fully apparent from the following description and appended claims, or may be learned by the practice of the invention as set forth hereinafter.

BRIEF DESCRIPTION OF THE DRAWINGS

These and other more detailed and specific features of the present invention are more fully disclosed in the following specification, with reference to the accompanying drawings, in which.

DETAILED DESCRIPTION OF THE PREFERRED EMBODIMENTS

Embodiments of devices and methods of use for a high pressure neon arc lamp are described herein. The embodiments of the present invention will be best understood by reference to the drawings, wherein like parts are designated by like numerals throughout.

In the following description, numerous specific details are provided, such as examples of devices, components, materials, sizes, configurations, and the like, to provide a thorough understanding of embodiments of the invention. One skilled in the relevant art will recognize, however, that the invention may be practiced without one or more of the specific details, or with other components, materials, devices, materials, etc. In other instances, well-known structures, materials, or operations are not shown or described in detail to avoid obscuring aspects of the invention.

Reference throughout this specification to "one embodiment" or "an embodiment" means that a particular feature, structure, or characteristic described is included in at least one embodiment of the present invention. Thus, references to embodiment or aspect throughout this specification are not necessarily all referring to the same embodiment. Furthermore, the particular features, structures, or characteristics may be combined in any suitable manner.

Figure 1:
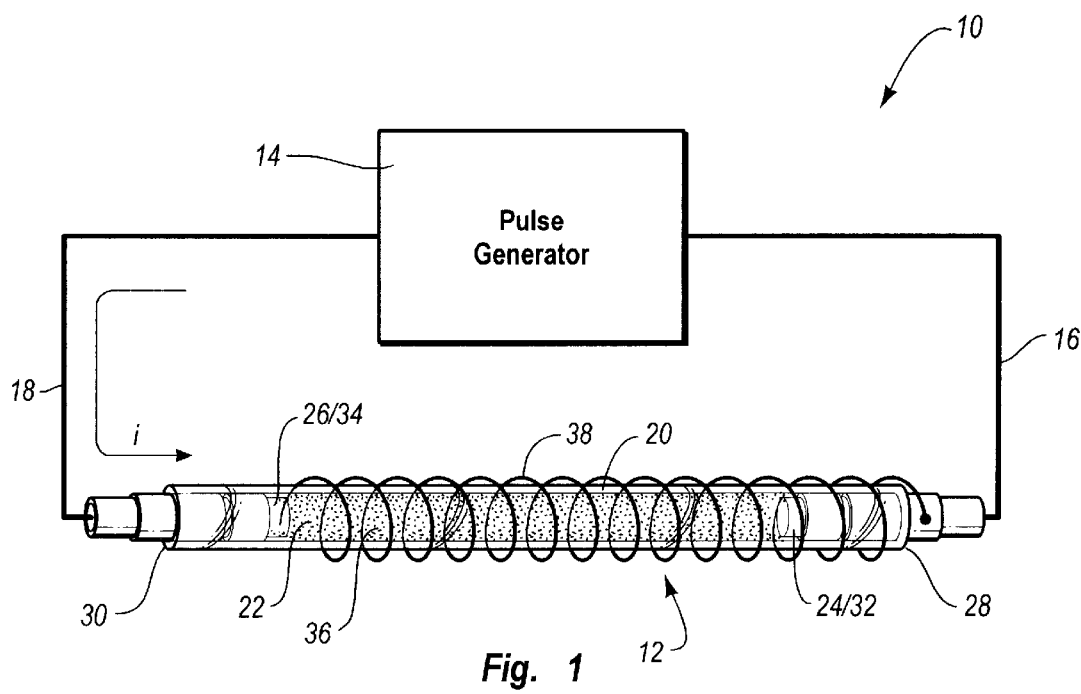
FIG. 1 is a perspective view of a high pressure neon arc lamp electrically coupled to a pulse generator for generating light having wavelengths from about 625 nanometers to about 645 nanometers.

Referring now to FIG. 1, a neon arc lamp system 10 configured to operate a high pressure neon arc lamp 12 is illustrated in a perspective view. The neon arc lamp system 10 will now be described in detail. The neon arc lamp system 10 provides electrical components for causing an electrical arc to pass through the high pressure neon arc lamp 12.

The system 10 includes a pulse generator 14. The pulse generator 14 provides a voltage pulse to overcome electrical impedance of the neon gas. The pulse generator also provides voltage and current for producing an electrical arc through the lamp 12. The pulse generator 14 is electrically connected by a first wire 16 to one end of the lamp 12 and by a second wire 18 to the other end of the lamp 12. The first wire 16 and second wire 18 enable electricity to flow in series from the pulse generator 14 to the lamp 12 and back to the pulse generator 14.

The lamp 12 includes a housing 20 configured to contain a quantity of neon gas. The housing 20 provides the main structure for the lamp 12. Preferably, the housing 20 is made from a solid piece of material and includes a bore 22 positioned coaxially to the longitudinal axis of the housing 20. The bore 22 runs from one end of the housing 20 to the other. Alternatively, the housing 20 and bore 22 may be fabricated using other conventional techniques such as extrusion, glass blowing, rolling, injection molding, and the like.

Preferably, the housing 20 is made from a translucent material such as quartz, glass, plastic, or the like. In a preferred embodiment, the housing 20 is made from an alumina silicate glass to provide the desired tensile strength and ensure integrity of the housing 20 during operation of the lamp 12. Alternatively, the housing 20 may be made from other glass, plastic, quartz, or other material compositions that provide a translucent housing 20. Preferably, the material used for the housing 20 is capable of storing a gas under pressure in the range of between about 500 and about 22,000 Torr. Fabrication of the housing 20 may include baking it at a high temperature to drive out impurities in the material. By driving out the impurities the housing 20 is better able to provide the tensile strength and integrity necessary to house a gas pressurized within the described range.

The housing 20 includes a first electrode 24 and a second electrode 26. The first electrode 24 is electrically connected to the first wire 16 and extends from a first end 28 of the housing 20 into the bore 22. Similarly, the second electrode 26 is electrically connected to the second wire 18 and extends from a second end 30 of the housing 20 into the bore 22. Each electrode 24, 26 is secured to its respective end 28, 30 of the housing 20. In this manner, each electrode 24, 26 is secured to an end of the bore 22.

In a preferred embodiment, the electrodes 24, 26 are made from different combinations of materials based on whether the electrode 24, 26 serves in the system 10 as a cathode 32 or an anode 34. In the illustrated embodiment of FIG. 1, the system 10 is configured such that the first electrode 24 is a cathode 32 and the second electrode 26 is an anode 34. However, the cathode 32 and anode 34 are so designated due to the configuration of the electrical circuit connected to the electrodes 24, 26. For example, if the first wire 16 is connected to the second electrode 26 and the second wire 18 is connected to the first electrode 24, then the first electrode 24 would become the anode 34 and the second electrode 26 would become the cathode 32. Similarly, the electrode 24, 26 designated as the cathode 32 and anode 34 may change as the current changes direction as may occur in certain embodiments.

The anode 34 and cathode 32 are made from conductive materials that facilitate arcing between the anode 34 and the cathode 32. Examples of such materials include tungsten, thoriated tungsten, barium aluminate impregnated porous tungsten, copper, copper alloys, and the like. The anode 34 and cathode 32 may be made from material having similar or different compositions.

Referring still to FIG. 1, the housing 20 is filled with neon gas 36. The neon gas 36 fills the bore 22 between the two ends 28, 30 of the housing 20. Preferably, the neon gas 36 is a substantially pure gas comprising essentially neon. Alternatively, neon gas 36 may be combined with other gases such as xenon, krypton and the like.

Preferably, the neon gas 36 is sealed within the bore 22 of the housing 20 under a constant pressure. Using conventional pressurizing and sealing techniques, neon gas 36 is placed inside the bore 22 and pressurized to a pressure of from about 500 Torr to about 22,000 Torr. Then, the housing 20 is sealed at both ends 28, 30 using conventional sealing techniques such as a tungsten-rod seal, solder seal, or the like. These techniques seal the neon gas 36 within the bore 22 and the electrodes 24, 26 to each end 28, 30 of the housing 20.

The neon arc lamp system 10 includes a pulse generator 14. The pulse generator 14 provides the electrical power to light the neon arc lamp 12. In one embodiment, the pulse generator 14 provides a voltage pulse and a current through the lamp 12. Alternatively, the pulse generator 14 may provide a continuous wave of current oscillating between positive and negative magnitudes to pass through the lamp 12. The pulse generator 14 preferably provides a plurality of voltage pulses at a particular rate. Alternatively, the pulse generator 14 may produce a single voltage pulse. Preferably, the voltage pulse rate depends on the light output power desired. The higher the desired power output is, the higher the voltage pulse rate will be and vice versa. The voltage pulse may be at a rate between 1 and 120 Hertz. In one embodiment, the voltage pulse rate is adjustable.

The voltage pulse generates a voltage differential between the first electrode 24 and the second electrode 26 of the lamp 12. Preferably, the voltage pulse delivers a voltage in the range from about 24 kilovolts to 30 kilovolts. The voltage pulse travels through the first wire 16 to the cathode 32 of the lamp 12. The purpose of the voltage pulse is to overcome, or "breakdown," the natural impedance to carrying of electrical current inherent in the neon gas 36 within the lamp 12.

The pulse generator 14 is connected on one end to the first wire 16 and on the other end to the second wire 18. The first wire 16 and second wires 18 are preferably both made from similar conductive material capable of carrying current in the range of about 100 to about 200 amperes and voltage in the range from about 24 kilovolts to about 30 kilovolts. Examples of such materials include copper, copper alloys, iron, and other similar conductive materials.

To facilitate breakdown of the impedance, the lamp 12 preferably includes a corona wire 38. Corona wires 38 are used conventionally to breakdown the impedance of gases for carrying of current. Although a corona wire 38 is used in the illustrated embodiment, the corona wire 38 is not necessary. Alternatively, the voltage pulse may be increased to overcome the natural impedance of the neon gas 36.

Preferably, the corona wire 38 is electrically connected to the cathode 32 of the lamp 12. The corona wire 38 is wrapped in a helical manner around the housing 20. The corona wire 38 extends from the cathode 32 towards the anode 34 for substantially the length of bore 22. The corona wire 38 is made from a conductive material such as metal.

The voltage pulse from the pulse generator 14 travels through the corona wire 38. The voltage applied to the corona wire 38 ionizes neon gas 36 in the vicinity of the corona wire 38. The ionization of a gas, such as neon 36, lowers its impedance. This induced ionization is commonly referred to as a corona discharge.

Shortly, after the impedance of the neon gas 36 is lowered, current i (indicated by the conventional lower case i and arrow) flows from the second wire 18 through the neon gas 36 to the first wire 16 and back into the pulse generator 14. The amount of current i that flows depends largely on the voltage and the conductive properties of the "broken down" neon gas 36. Preferably, the current flow i is in the range from about 100 to about 200 amperes.

The flow of current i between the anode 34 and the cathode 32 of the lamp 12 creates an electrical arc. The electrical arc emits photons. A majority of the photons have wavelengths between about 625 nanometers and about 645 nanometers. Light having these wavelengths is useful in photodynamic therapy applications (PDT).

Figure 2A:
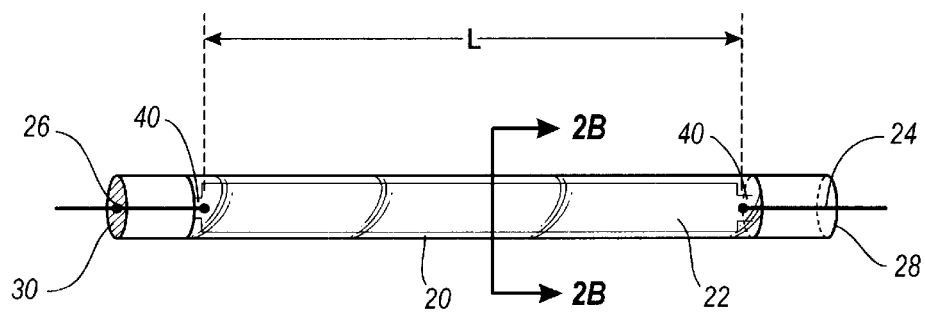
FIG. 2A is a perspective side view of the high pressure neon arc lamp.

Referring now to FIG. 2A, a perspective side view of the high pressure neon arc lamp 12 is illustrated. Preferably, the housing 20 has a straight cylindrical shape. Alternatively, the housing 20 may be prism shaped. The prism shape may be a cube, a cone, a torroid, or other geometric shape. In one embodiment, the housing 20 may be cylindrical and bent in the shape of helix rather than straight.

Generally, the bore 22 is a hollow area within the housing 20 that is formed by removing housing material. Preferably, the bore 22 is positioned coaxially to the longitudinal axis of the housing 20. As illustrated in FIG. 2A, the length L of the bore 22 extends substantially from the first end 28 of the housing 20 to the second end 30. Preferably the bore 22 has a constant diameter along its entire length L. Alternatively, the diameter may vary along the length L. At both ends 28, 30 of the housing 20 the electrodes 24, 26 are exposed to the bore 22 in a set back area 40. Length L generally represents the distance an electrical arc must travel to pass through the neon gas 36 between the electrodes 24, 26.

Figure 2B:
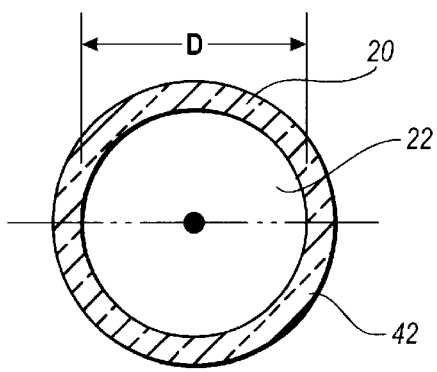
FIG. 2B is a cross-sectional view of the high pressure neon arc lamp illustrating the diameter of the bore.

Referring now to FIG. 2B, diameter D illustrates the diameter of the bore 22. Preferably, the ratio of the bore diameter to the bore length L ranges from about 1:10 to about 1:30. In a preferred embodiment, the diameter D is greater than 2 millimeters and the length L is greater than 2 centimeters. Preferably, the impedance of the lamp 12 is increased by increasing the length L. The higher impedance allows more energy to be deposited into the gas. The higher the energy deposited into the gas, the more light is created when an arc passes between the electrodes 24, 26.

FIG. 2B also illustrates a wall 42 that surrounds the bore 22. The wall 42 keeps the neon gas 36 within the bore 22 at the desired pressure. The wall 42 is preferably translucent to allow light from the electrical arc to exit the bore 22.

As an electrical arc travels the length L of the bore 22 through the neon gas radiation is emitted in all directions. The radiation generally comprises two primary types: (1) discrete; and (2) continuum. Photons generated by electrons of the neon gas atoms moving from an excited state to a lower state comprise discrete radiation. These photons are created at various times resulting in incoherent light exiting the housing 20. Incoherent light is comprised of photons that are not in phase with each other. Discrete radiation has a discrete amount of energy which results in a discrete wavelength and frequency. Continuum radiation comprises photons with wavelengths that vary along the electromagnetic spectrum.

Conventionally, production of discrete radiation having wavelengths in the range from about 625 nanometers to about 645 nanometers is accomplished using xenon or krypton in an arc lamp. However, the intensity of light created in the desired wavelengths is small in comparison to the energy passed through the lamps. This is due in part to the fact that the wavelengths of the majority of light generated by xenon and krypton arc lamps are shorter than 625 nanometers and fall within the ultra-violet range.

By contrast, the present invention is capable of producing light having wavelengths between about 575 nanometers and about 695 nanometers with minimal ultra-violet light. The most intense light produced by the neon arc lamp 12 comprises wavelengths between about 625 nanometers and about 645 nanometers. The high output of light having wavelengths within these ranges is due in part to the pressure of the neon gas 36 in the bore 22. The increased pressure raises the impedance within the lamp 12. The higher impedance allows more energy to be deposited into the neon gas. This energy is released when an arc passes between the electrodes 24, 26. The impedance may also be increased by increasing the volume within the bore 22 by increasing the length L. By increasing the impedance through higher pressure of the neon gas 36 and/or increased bore 22 volume, the intensity of light within the 625 nanometers to 645 nanometer wavelength range may be increased.

Figure 3:
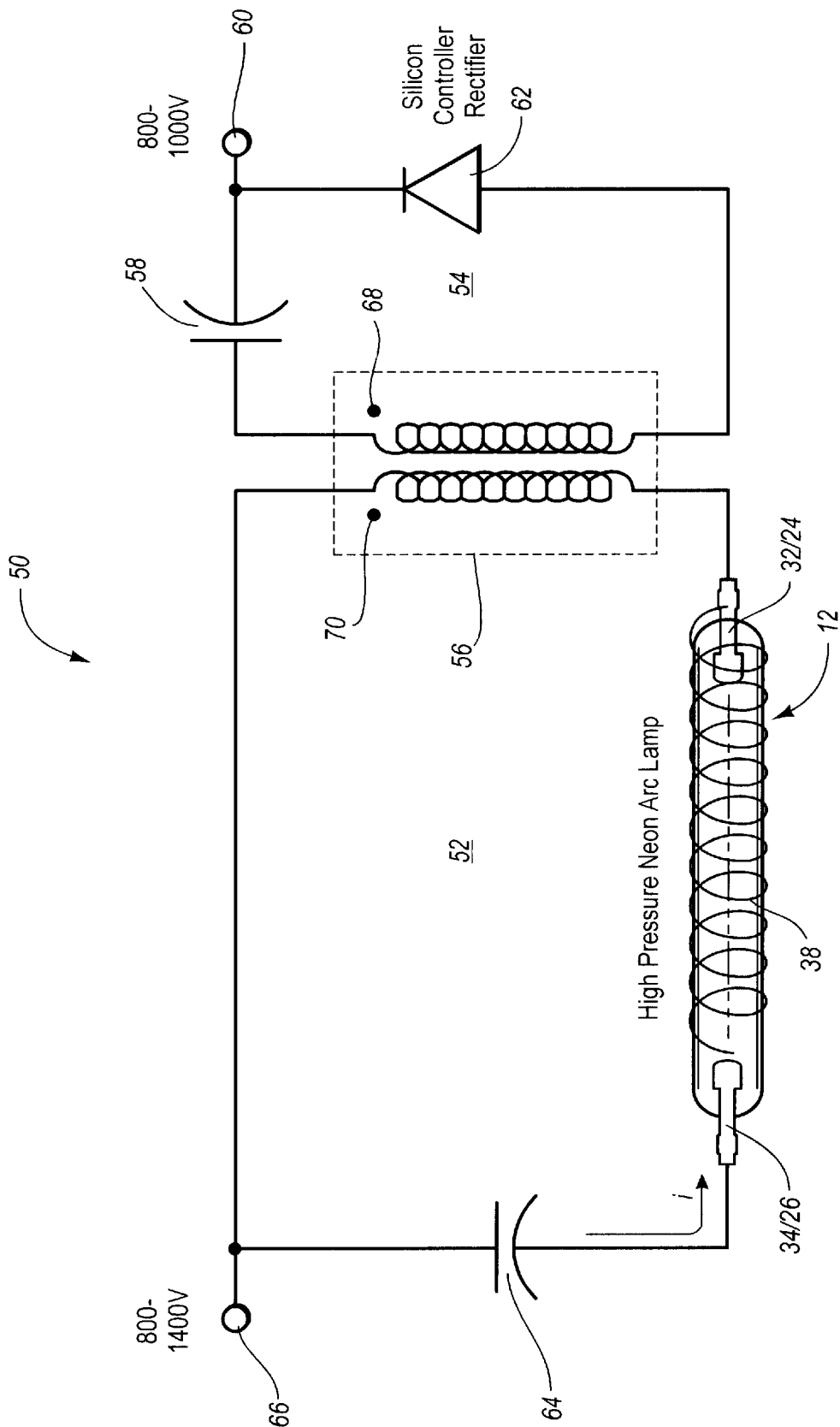
FIG. 3 is an electrical schematic diagram of one embodiment of the high pressure neon arc lamp.

Referring now to FIG. 3, an electrical circuit 50 is illustrated according to one embodiment of the present invention. Generally, the electrical circuit 50 exists within the pulse generator 14 and wires 16, 18 are connected to the high pressure neon arc lamp 12.

The circuit 50 includes a left-hand circuit 52 and a right-hand circuit 54. With the exception of the high pressure neon arc lamp 12, the left-hand circuit 52 and right-hand circuit 54 include well known electrical components. The left-hand circuit 52 and a right-hand circuit 54 are electrically coupled by a transformer 56. Preferably, the transformer 56 comprises a ratio of primary windings to secondary windings of about 1:30.

The right-hand circuit 54 includes (in clock-wise order) a first capacitor 58 connected in series to a first voltage source 60, a silicon controlled rectifier (SCR) 62, the transformer 56, and then back to the first capacitor 58. Preferably, the first capacitor 58 is configured to store one microfarad of electrical current. The first voltage source 60 is capable of providing voltages in the range from about 800 volts to about 1000 volts. The SCR 62 is a semiconductor that functions in the right-hand circuit 54 as an electrical switch. The SCR 62 is configured to open and close the right-hand circuit 54 at a rate of up to 100 Hertz or more.

The left-hand circuit 52 includes (in clock-wise order) the transformer 56 connected in series to the high pressure neon arc lamp 12, a second capacitor 64, and a second voltage source 66. Preferably, the high pressure neon arc lamp 12 has a configuration similar to that described above. The second capacitor 64 stores charge and has a capacitance of about ten microfarads. The second voltage source 66 provides voltage in a range from about 800 to about 1400 volts.

The process of delivering a voltage pulse and generating a single electrical arc will now be explained with general reference to FIG. 1, and specific reference to FIG. 3. Initially, first voltage source 60 and second voltage source 66 supply voltages in the ranges indicated through direct current to the respective right-hand circuit 54 and left-hand circuit 52. These voltages charge the first capacitor 58 to one microfarad and the second capacitor 64 to 10 microfarads. The first capacitor 58 and second capacitor 64 are at their full capacity. Next, the SCR 62 is triggered. Triggering the SCR 62 closes the right-hand circuit 54. This causes current i to flow from the first capacitor 58 into the transformer 56 at point 68.

The current i flows through the primary windings of the transformer 56 and induces a voltage in the secondary windings that is thirty times that of the voltage from the first voltage source 60. For example, if the first voltage source 60 provides about 1000 volts then the voltage induced in the secondary windings is about 30 kilovolts. The stepped up voltage in the secondary winding is the voltage pulse discussed earlier.

The voltage pulse in the secondary windings travels to the cathode 32 and into the corona wire 38. The high voltage pulse in the corona wire 38 causes a corona discharge around the wire 38. This discharge is an ionization of the gas, including both air around the lamp 12 and neon gas 36 within the housing 20 near the wire 38. (See FIG. 1).

Ionization of the neon gas 36 in the housing 20 causes free electrons to leave from the neon atoms within the bore 22 of the housing 20. These free electrons are accelerated by the voltage across the electrodes 24, 26. The free electrons gain energy and further energize other neon atoms which increases the current and decreases the resistance across the electrodes 24, 26 to a level below the charging voltage of the second voltage source 66. At this point, the stored energy in the second capacitor 64 is delivered to the neon arc lamp 12 in a low voltage arc. Then, the SCR 62 slowly recovers and becomes an open circuit. Accordingly, the first capacitor 58 begins to recharge.

The arc releases photons of discrete energy. The photons are released randomly and with wavelengths in the range from about 570 nanometers to 700 nanometers. The most intense photons are in the range from about 625 nanometers to about 645 nanometers. The light emitted is incoherent and appears red to an observer.

The amount of current i is preferably in the range from about 100 amperes to about 200 amperes. This amount of current is high enough to cause bound state emissions of photons from the neon atoms but low enough to minimize continuum radiation. Alternatively, current of other ranges may be supplied following initial "breakdown" of the neon gas. The amount of current supplied is directly related to the size of the second capacitor 64 and the voltage of the second voltage source 66.

Referring still to FIG. 3, in a preferred embodiment, the left-hand circuit 52 comprises a conventional series RLC circuit. The lamp 12 is the resistor, the secondary windings of the transformer 56 comprise the inductor, and the second capacitor 64 is the capacitor. Accordingly, the current i may oscillate between the second capacitor 64 and the secondary windings of the transformer 56. With each oscillation, the current i passes through the high pressure neon arc lamp 12 creating an electrical arc. Each oscillation releases energy from the system in the form of heat and the photons created by the electrical arc. Therefore, the current i loses magnitude with each oscillation.

In a preferred embodiment, the current i oscillates until no current flows in the left-hand circuit 52 before the next voltage pulse is applied by the right-hand circuit 54. Alternatively, the current i may decrease in magnitude to approach substantially zero before the next voltage pulse is applied.

Figure 4:
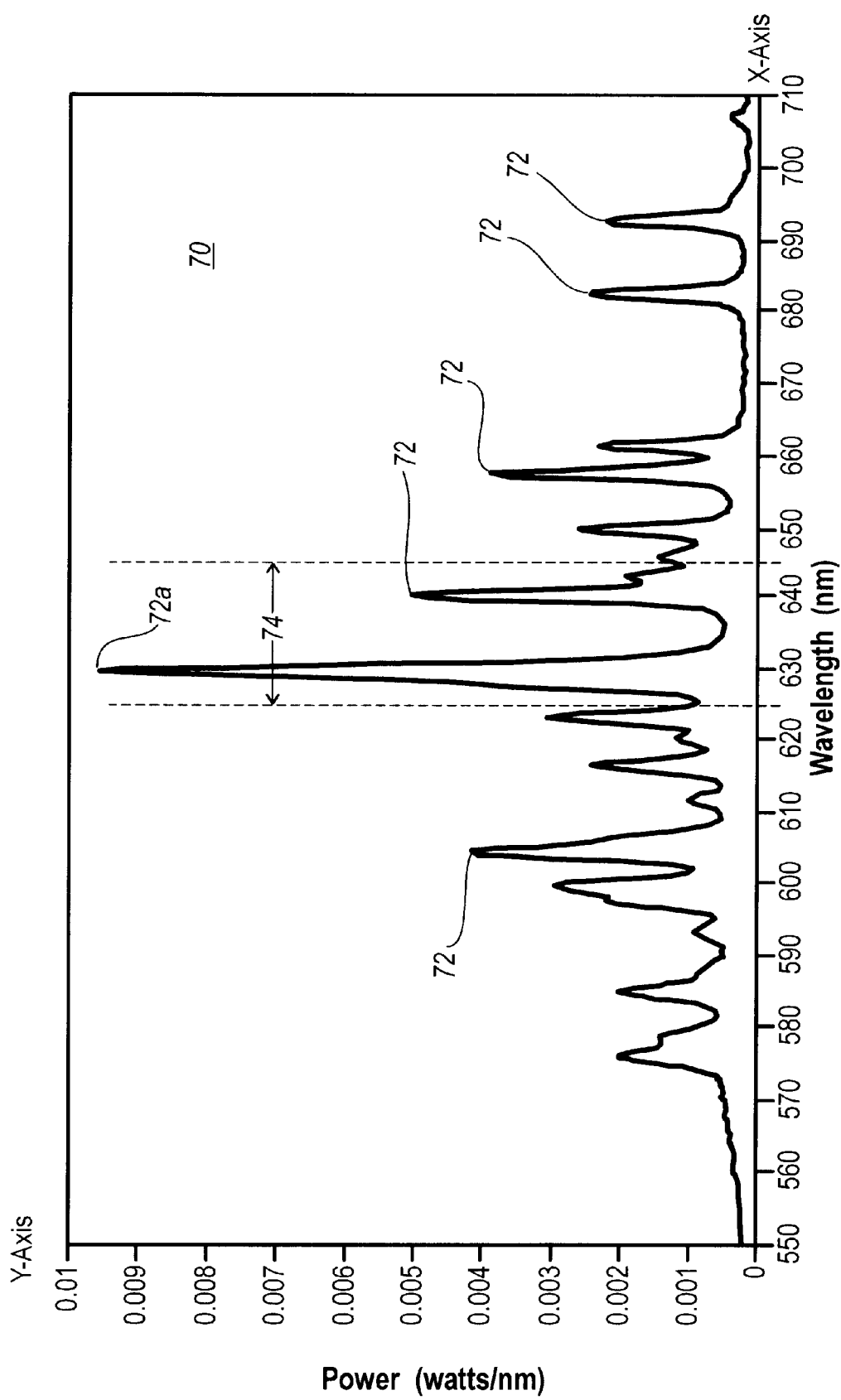
FIG. 4 is a graph illustrating the power produced by one embodiment of the high pressure neon arc lamp.

Referring now specifically to FIG. 4 and generally to FIG. 1, a graph 70 illustrates the power of light produced by a high pressure neon arc lamp 12 according to the present invention. Along the x-axis, the graph 70 indicates wavelength in nanometers. Along the y-axis, the graph 70 indicates power in watts per nanometer.

In one embodiment, the high pressure neon arc lamp 12 includes a cylindrical bore 22 with a 4 millimeter diameter and 6 centimeter length. Graph 70 illustrates the power output from such a configuration. The neon gas 36 within the bore 22 is pressurized to about 7600 Torr. The graph 70 illustrates both spectral lines and intensity of the spectral lines.

The peaks 72 represent the amount of power output by photons of the particular wavelength. For example, the maximum peak 72a has a wavelength of about 630 nanometers and produced almost 0.01 watts of power at that wavelength. The peaks 72 are very narrow and distributed along the x-axis according to the spectral line signature for neon.

Region 74 covers wavelengths from about 625 nanometers to about 645 nanometers. Region 74 represents the light wavelengths that are generally most effective in photodynamic therapy (PDT) applications. The average power of light in region 74 is about 0.169 watts. The efficiency of light production in region 74 is about 1.72%.

Light production efficiency is the average power generated per pulse in a wavelength region, i.e. region 74, divided by the energy used to produce the light. The energy to produce the light in this embodiment comes from the second capacitor 64. In graph 70, the energy in the second capacitor 64 is 9.8 joules (0.5CV↑2=0.5*10 microfarads*(1400↑2)). For region 74, the resulting efficiency is then 1.72% (0.169 watts/9.8 joules*100). This efficiency is very high in comparison to that of conventional xenon or krypton arc lamps for a similar region 74.

Referring generally to FIGS. 1, 2, and 4, in one embodiment, the high pressure neon arc lamp 12 containing substantially pure neon gas 36 pressurized between about 500 and about 22,000 Torr together with a pulse generator 14 configured to deliver between about 24 kilovolts to about 30 kilovolts to the lamp 12 may be used to activate photosensitive drugs. Light having wavelengths in region 74 is capable of activating photosensitive drugs such as Photofrin®, and the like. Photosensitive drugs together with a neon arc lamp system 10 have proven effective in treating lung, esophageal, cervical, bladder, gastric cancer and other diseases. Photosensitive drugs together with a neon arc lamp system 10 may also be used to treat acne, remove unwanted hair, and destroy antibiotic resistant pathogens.

Conventionally, photosensitive drugs are activated using red light, light having wavelengths of about 625 nanometers to about 645 nanometers, from lasers such as those used in medicine. However, medicinal lasers are generally very expensive and bulky. These expenses are often passed on to the patient. Additionally, lasers are generally designed to focus light. Therefore, the illumination area provided by a laser is generally very small in comparison to the treatment area.

In contrast, the shape and size of the high pressure neon arc lamp 12 provides a relatively large illumination area in comparison to that of most lasers. The size and shape of the lamp 12 are directly related to the size of the area the lamp 12 may illuminate. The size and shape of the lamp 12 depend on the size and shape of the housing 20.

For example, a cylindrical housing 20 with a bore that is 10 centimeters in length and a 4 millimeter diameter may be used in a device to activate photosensitive drugs. The electrical arc causes light to be emitted along the length of the bore 22. With this configuration, the high pressure neon arc lamp 12 illuminates an area of 100 square centimeters, 10 centimeters by 10 centimeters. The illumination power is about 100 milliwatts per square centimeter for light having wavelengths from 625 nanometers to 645 nanometers. Such illumination areas may be useful in activating photosensitive drugs for the treatment of cancer, removal of hair, acne, and other diseases, particularly those with large affected areas such as skin diseases.

A method for using the high pressure neon arc lamp system 10 will now be described. First, a photosensitive drug, also known as a photosensitizer, such as Photofrin® is administered to a patient. Generally, administration is done intravenously.

Then, the photosensitizer is allowed to be absorbed by target tissue within the patient. Target tissue is one or more cells or organisms within the patient that the PDT treatment is designed to destroy. Target tissue may include cancerous cells, hair follicle cells, and other diseased cells, or disease causing organisms. The absorption step may take from several hours to a few days depending on the nature of the disease and the location of the target cells.

Next, the target tissue is illuminated using the high pressure neon arc lamp 12. Light with wavelengths between 625 nanometers and 645 nanometers leaves the lamp 12 and enters the body of the patient to illuminate the target tissue. When the light activates the photosensitizer, the photosensitizer destroys the target tissue. Destruction of the target tissue may be accomplished by the photosensitizer generating a oxygen free radical that destroys the target tissue. In this manner, the target tissue is destroyed with minimal invasion of the patient's body.

Figure 5:
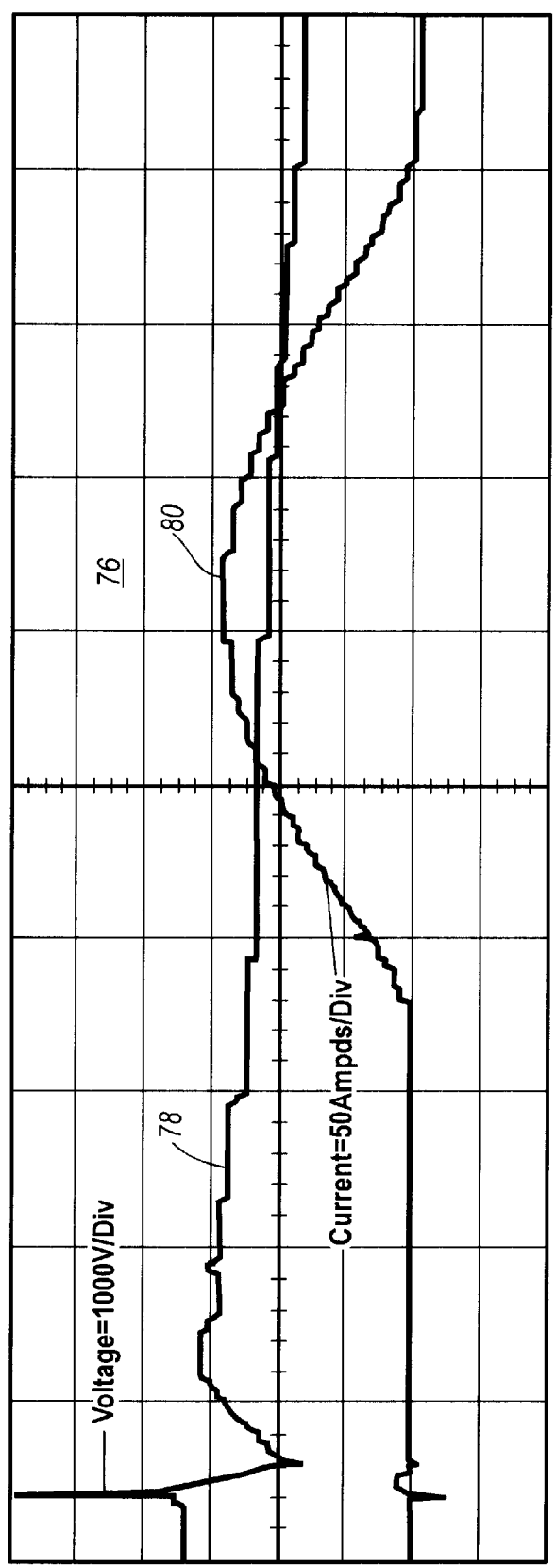
FIG. 5 is a graph illustrating voltage and current as a single voltage pulse is delivered through the high pressure neon arc lamp.

Referring specifically to FIG. 5 and generally to FIGS. 1 and 3, graph 76 illustrates voltage and current for one embodiment of the present invention. The y-axis indicates both voltage and current. The x-axis indicates time. Voltage is 1000 volts per y-axis division. Current is 50 amperes per y-axis division. The graph 76 includes a voltage curve 78 and a current curve 80.

The voltage curve 78 illustrates that the voltage spikes initially and then drops as the impedance of the lamp 12 is "broken down." After the lamp 12 breaks down, the voltage curve 78 gradually begins to approach zero. The voltage spike represents the voltage pulse discussed above.

The current curve 80 is generally flat until after the impedance in the lamp 12 is "broken down." Then the current curve 80 begins to rise. In this sample data, the current rises to about 150 amperes. The rise in current is caused by electrical energy from the second capacitor 64 going into the lamp 12. The current then passes from the anode 34 to the cathode 32 as an electrical arc that gives off light. Current curve 80 approaches zero as the energy is drained from second capacitor 64.

In certain embodiments, the current flows back through the lamp in reverse order. This is caused by the inductance created by the secondary windings of the transformer 56. The current may then create another electrical arc as it travels in reverse from the first electrode 24 to the second electrode 26 and recharges the second capacitor 64. Similarly, the current may again pass from the second capacitor 64 through the lamp 12 to the transformer 56. With each pass through the lamp 12 a portion of the current is dissipated as heat and light. In one embodiment, the current dissipates to zero before a subsequent voltage pulse is applied. Alternatively, the current may make a single pass through the lamp 12 before a subsequent voltage pulse is applied.

Figure 6:
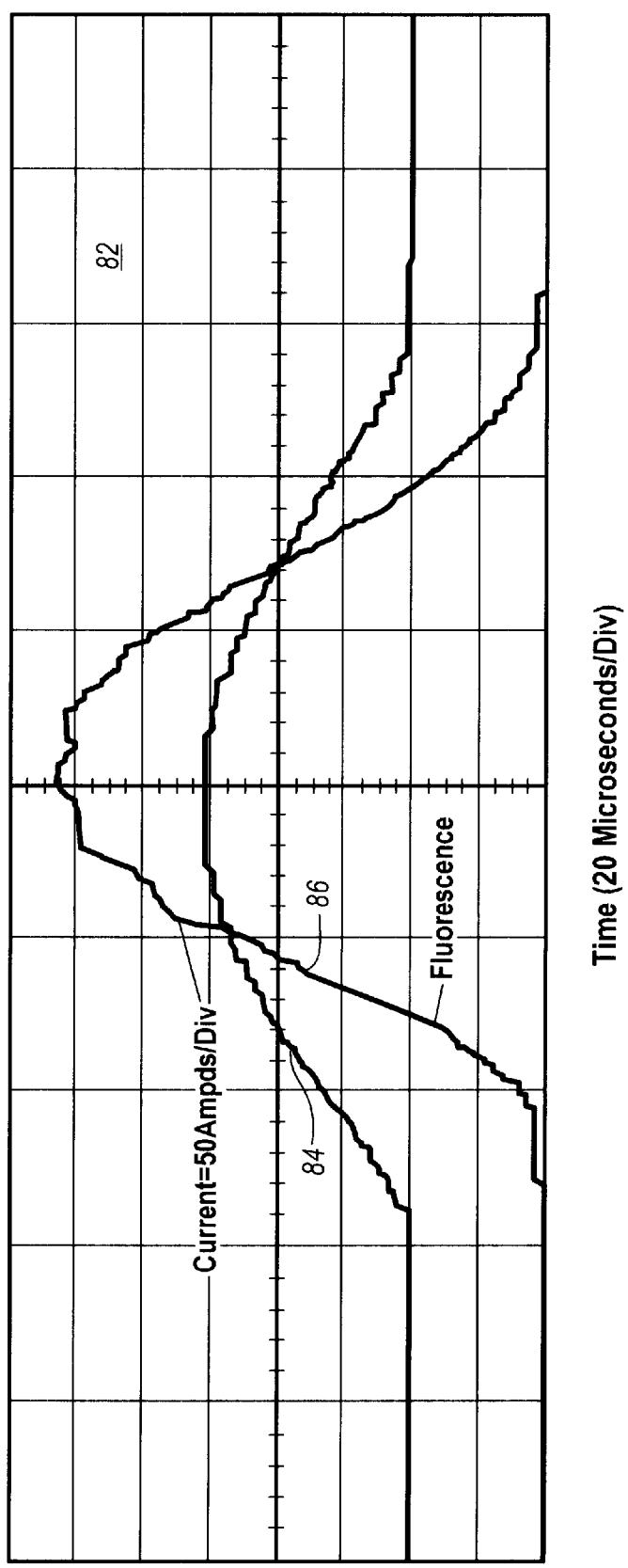
FIG. 6 is a graph illustrating current and fluorescence when the electrical arc is produced through the high pressure neon arc lamp.

Referring now to FIG. 6, a graph 82 illustrates a current curve 84 in relation to a fluorescence curve 86. The x-axis represents time intervals. The y-axis represents magnitudes. The slope of the fluorescence curve 86 illustrates that the electrical arc occurs and emits light when the current curve 84 is rising. The fluorescence curve 86 represents a comparison of light output from the electrical arc to that of a standard tungsten lamp at a given distance from the source in accordance with National Institute of Standards and Technology (NIST) standards.

The present invention provides a high pressure neon arc lamp and method of use that produces photons in the red band of the electromagnetic spectrum, light having wavelengths between about 625 nanometers and about 645 nanometers, with minimal power requirements. The present invention provides a light source for activating photosensitizers that is less expensive to fabricate than conventional laser devices. Additionally, the present invention provides a photosensitive drug activation device that provides a comparably large illumination area to that of conventional red light sources.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A neon arc lamp comprising:
   a translucent housing having a substantially cylindrical bore wherein the ratio of the diameter of the bore to the length of the bore is in the range from about 1:10 to about 1:30; and
   a quantity of substantially pure neon gas contained within the bore and having a pressure of about 500 Torr to about 22,000 Torr.

2. The neon arc lamp of claim 1, wherein the diameter of the bore is about 4 millimeters to about 6 millimeters.

3. The neon arc lamp of claim 2, wherein the length of the bore is between about 4 centimeters and about 12 centimeters.

4. The neon arc lamp of claim 1, further comprising a first electrode secured at one end of the bore and a second electrode secured at an opposite end of the bore.

5. The neon arc lamp of claim 4, wherein the first electrode is a cathode and the second electrode is an anode.

6. The neon arc lamp of claim 4, further comprising a pulse generator configured to apply a voltage between the first electrode and the second electrode to cause an electrical arc between the first electrode and the second electrode.

7. The neon arc lamp of claim 6, wherein the voltage is in the range of about 24 kilovolts to 30 kilovolts.

8. The neon arc lamp of claim 6, wherein the pulse generator is configured to produce a pulse of voltage at a rate of about 1 to 100 Hertz.

9. The neon arc lamp of claim 6, wherein the electrical arc produces incoherent light having wavelengths between about 625 nanometers and about 645 nanometers.

10. The neon arc lamp of claim 6, further comprising a helical corona wire wrapped around the housing, attached to the first electrode, and extending from the first electrode.

11. The neon arc lamp of claim 10, wherein the helical corona wire creates a corona discharge in the quantity of neon gas to lower impedance between the first electrode and the second electrode to allow current in the range from about 100 amperes to about 200 amperes to pass between the first electrode and the second electrode.

12. A photosensitive drug activation device comprising:
   a high pressure neon arc lamp configured to generate light having wavelengths between about 625 nanometers and about 645 nanometers, wherein neon gas within the high pressure neon arc lamp has a pressure in the range from about 500 Torr to about 22,000 Torr; and
   a pulse generator configured to pass voltage through the high pressure neon arc lamp in the range from about 24 kilovolts to about 30 kilovolts.

13. The photosensitive drug activation device of claim 12, wherein the high pressure neon arc lamp is further configured to produce an average power of 0.169 watts at a pulse rate of about 1 Hertz within the wavelengths.

14. The photosensitive drug activation device of claim 13, wherein the pulse generator generates a voltage pulse at a rate of between about 1 Hertz to about 100 Hertz.

15. The photosensitive drug activation device of claim 14, wherein current of between about 100 amperes and about 200 amperes passes through the high pressure neon arc lamp.

16. A method for activating photosensitizers using incoherent light having wavelengths from about 625 nanometers to about 645 nanometers, the method comprising:
   administering a photosensitizer to a patient;
   allowing the photosensitizer to be absorbed by target tissue of the patient; and
   illuminating the target tissue using a high pressure neon arc lamp comprising substantially pure neon having a pressure in the range of about 500 Torr to about 22,000 Torr to initiate generation of an oxygen free radical to destroy the target tissue.

17. The method of claim 16, wherein the high pressure neon arc lamp comprises a translucent housing having a substantially cylindrical bore wherein the ratio of the diameter of the bore to the length of the bore is in the range of from about 1:10 to about 1:30.

18. The method of claim 16, wherein the target tissue is cancerous cells.

19. The method of claim 16, wherein the target tissue is hair follicle cells.

* * * * *